(12) United States Patent
Offermans et al.

(10) Patent No.: US 9,038,437 B2
(45) Date of Patent: May 26, 2015

(54) CHEMICAL SENSOR HAVING A FLEXIBLE MEMBER WITH III/N HETEROJUNCTION

(71) Applicant: Stichting IMEC Nederland, Eindhoven (NL)

(72) Inventors: Peter Offermans, Eindhoven (NL); Roman Vitushinsky, Vaals (NL); Mercedes Crego Calama, Geldrop-Mierlo (NL); Sywert Brongersma, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 407 days.

(21) Appl. No.: 13/666,356

(22) Filed: Nov. 1, 2012

(65) Prior Publication Data

US 2013/0111977 A1 May 9, 2013

(30) Foreign Application Priority Data

Nov. 4, 2011 (EP) .................................... 11187960

(51) Int. Cl.
*G01N 27/04* (2006.01)
*G01N 27/12* (2006.01)
*G01N 33/00* (2006.01)

(52) U.S. Cl.
CPC .......... *G01N 27/128* (2013.01); *G01N 33/0009* (2013.01); *G01N 27/129* (2013.01)

(58) Field of Classification Search
CPC .. G01N 27/12; G01N 27/128; G01N 33/0009
USPC ........................................................ 73/31.06
See application file for complete search history.

(56) References Cited

U.S. PATENT DOCUMENTS

| | | | |
|---|---|---|---|
| 7,403,113 B2 * | 7/2008 | Moon et al. | 340/539.22 |
| 8,828,713 B2 * | 9/2014 | Ren et al. | 435/287.2 |
| 8,835,984 B2 * | 9/2014 | Ren et al. | 257/194 |
| 2005/0034529 A1 * | 2/2005 | Tang et al. | 73/777 |
| 2005/0263790 A1 * | 12/2005 | Moon et al. | 257/194 |
| 2009/0174014 A1 | 7/2009 | Kunze et al. | |

(Continued)

OTHER PUBLICATIONS

Hung, Ching-Wen et al., "Study of a New Field-Effect Resistive Hydrogen Sensor Based on a Pd/Oxide/AlGaAs Transistor", IEEE Transactions on Electron Devices, vol. 52, No. 5, May 2007, pp. 1224-1231.

(Continued)

*Primary Examiner* — Peter MacChiarolo
*Assistant Examiner* — Nathaniel Kolb
(74) *Attorney, Agent, or Firm* — McDonnell Boehnen Hulbert & Berghoff LLP

(57) ABSTRACT

The application describes methods and apparatus for chemical sensing, e.g. gas sensing, which have high sensitivity but low power operation. A sensor is described having a flexible membrane comprising a III/N heterojunction structure configured so as to form a two dimensional electron gas within said structure. A sensing material is disposed on at least part of the flexible membrane, the sensing material being sensitive to one or more target chemicals so as to undergo a change in physical properties in the presence of said one or more target chemicals. The sensing material is coupled to said heterojunction structure such that said change in physical properties of the sensing material imparts a change in stress within the heterojunction structure which modulates the resistivity of the two dimensional electron gas.

19 Claims, 3 Drawing Sheets

(56) References Cited

U.S. PATENT DOCUMENTS

2010/0188069 A1* 7/2010 Ren et al. .................. 324/71.5
2011/0068372 A1* 3/2011 Ren et al. .................. 257/194
2011/0074381 A1* 3/2011 Ren et al. .................. 324/71.5
2014/0120630 A1* 5/2014 REN et al. .................. 436/501

OTHER PUBLICATIONS

European Search Report, European Patent Application No. 11187960.7 dated May 2, 2012.
Brueckner, K. et al., "Two-Dimensional Electron Gas Based Actuation of Piezoelectric AlGaN/GaN Microelectromechnical Resonators", Applied Physics Letters, vol. 93, 2008, pp. 173504-1-173504-3.
Privorotskaya, Natalya et al., "The Mechanics of Polymer Swelling on Microcantilever Sensors", Microsyst Technol, vol. 15, 2009, pp. 333-340.
Blanchard, Roxann R. et al., "Hydrogen-Induced Piezoelectric Effects in InP HEMT's", IEEE Electron Device Letters, vol. 20, No. 8, Aug. 1999, pp. 393-395.
Pearton, S.J. et al., "GaN-Based Diodes and Transistors for Chemical, Gas, Biological and Pressure Sensing", Journal of Physics Condensed Matter, vol. 16, 2004, pp. R961-R994.

\* cited by examiner

CHEMICAL SENSOR HAVING A FLEXIBLE MEMBER WITH III/N HETEROJUNCTION

CROSS-REFERENCE TO RELATED APPLICATIONS

This application claims priority to European Patent Application no. 11 187 960.7, filed Nov. 4, 2011, which is hereby incorporated herein by reference in its entirety.

BACKGROUND OF THE INVENTION

1. Field of the Invention

The present invention relates to an apparatus and method for chemical sensing, and more specifically to gas detection sensors using heterostructures that form a two-dimensional electron gas channel.

2. Technical Background

Chemical sensing, such as gas detection, is required in a number of different applications such as in situ air pollution monitoring and industrial manufacturing. In many applications it is important that the sensors exhibit at least some of the following properties: being operable at room temperature; being relatively low cost; being suitable for use in a battery operated apparatus, i.e. having a low power consumption; being reliable and not subject to degradation; and having a fast response with a high sensitivity and resolution.

Ion sensitive FETs and gas FETs are known types of semiconductor based sensor that use a FET configuration with a conductive channel that responds to changes in the ion/gas concentration. In one arrangement changes in the ion/gas concentration result in a change in the potential formed between the gate and the channel. In gate-less configurations the sensors respond to charges or dipoles formed at the channel surface, by channel depletion or enhancement.

Recently, gas sensors based on heterostructures that form a high mobility two dimensional electron gas (2DEG) have been proposed. The 2DEG that forms in such structures provides a highly conductive channel that can be operated similar to the conventional FET based sensors, but with the advantage of a much higher electron mobility which can result in a higher sensitivity.

Hung et al. "Study of a New Field-Effect Resistive Hydrogen Sensor Based on a Pd/Oxide/AlGaAs Transistor", IEEE Transactions on Electron Devices, Vol. 52, No. 5, pp 1224-1231, May 2007 describes a hydrogen sensor with a Pd gate electrode on an oxide layer. Hydrogen dissociates at the surface of the Pd gate electrode and forms a dipole layer. The presence of a dipole layer causes a significant decrease in channel resistance in the 2DEG formed in an InGaAs layer. Such a structure can only be used however for sensing of a limited set of gases that can dissociate at the surface of certain metals.

MEMS resonator structures using 2DEGs have also been proposed as gas sensors. Patent application US2009/0174014 teaches a MEMS structure with a 2DEG that can be used as an actuator but which can also be used as a resonator coated with adsorbing or absorbing coating. Binding of the chemical species to the coating changes the resonance properties of the structure, for example due to a mass change of the resonator. Such a resonance structure can work with any suitable coating but requires the sensor to be constantly electrically actuated in use, which results in relatively high power consumption.

In certain aspects, the present invention aims to provide an improved apparatus and method for chemical sensing.

SUMMARY OF THE INVENTION

According to an exemplary embodiment of the invention there is provided a chemical sensor comprising: a flexible membrane comprising a III/N heterojunction structure configured so as to form a two dimensional electron gas within said structure; and a sensing material disposed on at least part of said flexible membrane, the sensing material being sensitive to one or more target chemicals so as to undergo a change in physical properties in the presence of said one or more target chemicals; wherein the sensing material is coupled to said heterojunction structure such that said change in physical properties of the sensing material imparts a change in stress within the heterojunction structure which modulates the resistivity of the two dimensional electron gas.

As will be described in more detail here below, the resistivity of a two dimensional electron gas (2DEG) in a III/N heterojunction structure can be influenced by the mechanical stress applied to the heterostructure. By using a flexible membrane structure for the 2DEG and using an additional sensing material that causes a mechanical compressive or tensile stress at the membrane surface due to, for example, swelling-solving, E-modulus changes and/or heating, in the presence of the target chemical(s), a high sensitivity and reliable sensor can be realised that provides sensing functionality for a wide variety of target chemicals and which does not require electrical actuation and thus offers low power operation. By the interaction of one or more target chemicals with the sensing material deposited on the flexible membrane, the material (e.g. a polymer) undergoes structural changes mentioned above affecting the 2DEG charge carrier density and therefore its electrical conductivity due to the stress-induced piezoelectric-piezoresistive effect starting at the adhesion interface of the sensitive material.

Whilst any suitable III/N materials, i.e. group III nitride compounds, may be used, the heterojunction may, in particular, comprise a first layer of AlGaN and a second layer of GaN. AlGaN/GaN is a chemically stable and biocompatible material which can be grown on conventional Si substrates, enabling lower cost and compatibility with conventional processing techniques.

Advantageously the first layer of AlGaN may be a relatively thin layer, for instance the first layer of AlGaN may have a thickness in the range of 5-20 nm inclusive, or a thickness in the range of 6-10 nm inclusive. The use of a thin AlGaN layer can improve sensitivity. Advantageously the second GaN layer is thick enough to provide structural rigidity but thin enough that the membrane remains flexible. For instance the GaN layer may have a thickness in the range of, 500 nm-3 μm inclusive or within the range of 1-2 μm inclusive.

It should be noted that, as used in the present specification, the term "flexible" shall be taken to mean that the membrane is able to bend or otherwise significantly deform in response to strains of the order of those induced by the change in physical properties of the sensing material.

In one embodiment the flexible membrane is connected to side walls at its edges and is suspended relative to a substrate. The membrane may be suspended over the substrate, so as to define a cavity between the membrane and substrate, or else the membrane may be suspended relative to a substrate around the sides of the membrane. The side walls may therefore extend above and/or below the membrane and thus the area above and/or below the membrane may comprise a recess. Such an arrangement can be useful when adding the sensing layer as the sensing material can be deposited on the membrane within the recess and the side walls prevent loss of material during deposition. In one embodiment the membrane is circular in shape. As will be described in more detail later a circular membrane may have advantages in manufacture. It should be noted that the membrane does not necessarily form a continuous structure with the supporting structure, i.e. there may be gaps within the membrane or between the edges of the membrane and any surrounding structure. Thus the membrane may form part of a bridge or beam structure.

For use, the sensor will be provided with readout circuitry for determining and monitoring the resistance of the two-dimensional electron gas channel. As only a relatively simple measurement of the 2DEG electrical resistance is required, the readout circuitry may be a direct current (DC) readout without AC-DC conversion. The power consumption of the sensor is thus significantly lower than sensors based on actuated MEMS resonator structures. In one embodiment the readout circuitry may comprise first and second electrodes disposed such that the two dimensional electron gas provides a conductive path between said first and second electrodes; and circuitry for generating a DC current between said electrodes and monitoring at least one of the magnitude of said DC current and a DC voltage between the first and second electrodes. The readout circuitry may, for example, drive a DC current and measure the resulting voltage or apply a DC voltage and measure the current that flows.

The sensing material may be any material which is sensitive to the desired target chemical(s) to provide a change in properties which can result in a change in stress in the flexible membrane. For instance, the change in physical properties of the sensing material may be a volume change (e.g. by swelling, shrinking, expansion or compression) due to absorption of the one or more target chemicals or a change in structure or amount of the sensing material due to absorption and/or dissolution of the sensing material in the presence of the one or more target chemicals. Thus, for example, the sensing layer may experience absorption-induced swelling or shrinking (due to, for example, molecule chain packaging changing) in the presence of the target chemical(s). The deformation of the sensing material is mechanically transformed through the adhesion interface to the flexible membrane thereby causing a mechanical stress and, accordingly, a piezoresistive-piezoelectric based modulation of the 2DEG-conductivity.

It should be noted that the change of physical properties of the sensing material may therefore be arranged to increase or reduce the stress in the flexible membrane. The sensor may therefore be arranged such that, in the absence of any of said one or more target chemicals, said flexible membrane is in a stressed state. In other words the sensor may be fabricated such the flexible membrane is in a pres-stressed state.

In one embodiment the heterojunction is configured such that the 2DEG is formed along a path within the flexible membrane, the path being configured to run through regions of the membrane that experience high stress in response to the change in physical properties of the sensing material. As will be appreciated by one skilled in the art the 2DEG will be formed along a defined channel based on the pattern of the heterojunction layers and/or doping regions. The path may then be arranged to run through regions of the flexible membrane that, in use, experience the greatest change in stress. For example considering a circular membrane held which is held by side walls around its edges any bending caused by say swelling of the sensing material layer may result in the greatest stress around the edges of the membrane, near to the side walls. The path of the 2DEG channel may therefore be arranged to pass generally around the edges of the membrane.

In still another embodiment the heterojunction is configured such that the 2DEG channel is formed along a path within the flexible membrane and designed with predetermined dimensions such as to ensure a certain heating temperature of the flexible membrane when a certain current is applied across said channel. This is advantageous since the formed 2DEG channel can be then used also to heat, any specific part of the chemical sensor structure, to a certain temperature in order to enable sensing, improve its sensitivity and/or selectivity and/or induce sensor recovery. This avoids the need to add an external heating element to the chemical sensor in order to heat any part of the chemical sensor structure in order to change its sensing properties and therefore advantageously decreases the manufacturing complexity and/or cost of the sensor. According to an embodiment, the sensor structure itself is used to provide heating or self-heating of the sensor. The 2DEG channel fabricated in the flexible membrane allows the direct heating, for example, of the channel surface itself, by the application of a sufficiently high voltage or current across the channel. Advantageously the heating occurs locally on the surface of the membrane (without a big heat transfer/loss to the substrate), so that the surface of the stack is heated very effectively, and allows thermally induced desorption of the gas molecules and reaction products that cover the surface. Advantageously, since the 2DEG channel is formed in a suspended membrane over a substrate, the electrical power needed for heating the sensor to a certain temperature is further reduced. By removing the silicon underneath the flexible membrane, heat loss to the substrate is substantially reduced and the region of the sensor that is heated is increased. In an embodiment, the membrane comprises a 2DEG channel that is advantageously highly conductive, which further reduces electrical power needed for sensor heating. In an embodiment, in order to increase the efficiency of heating at low power, the dimensions, for example the width and/or length of the channel, may be designed such as to achieve low resistance and small surface area. Furthermore, the application field of the sensor may require a certain heating temperature enabling chemical recovery thresholds, for example, in one embodiment, a chemical sensor for detecting $NO_2$ works at room-temperature and needs to be heated to a temperature around or higher 100 C to allow a fast recovery of the sensor, i.e. by thermal induced desorption of molecules from the surface.

The sensing material may comprise a layer of sensing material located on a top side of the flexible membrane and/or a layer of sensing material located on a bottom side of the flexible membrane. As mentioned above if one side of the membrane is effectively located in a depression below some side wall such a surface may be preferred for the sensing material as deposition may be easier and/or require less material. However either or both surface of the membrane may carry a layer of sensing material provided that the layer of sensing material can be exposed to an analyte. If both surfaces of the membrane are coated in sensing material the layers should be arranged so that the change in physical properties of both layers add to the same change in stress, rather than cancel each other out.

It should be noted that the sensor may be used in gas detection, for instance for detecting $NO_x$, CO, $NH_3$, $H_2S$, $CO_2$, toluene, benzene, formaldehyde, or alcohols but the sensor may also be used in liquid based sensing, using suitable swellable polymers as the sensing material for various chemicals of interest. Thus the sensor could be deployed in use with the flexible membrane within or adjacent a liquid analyte. It will be appreciated that resonant sensor which rely on resonance of MEMS structure are not typically able to operate in liquid environments due to the strong damping due to the liquid.

In use, the sensor may be incorporated as part of a chemical sensor system including control circuitry wherein the sensor system is configured to detect the presence of the one or more target chemicals by detecting stress induced resistivity modulation of the two dimensional electron gas.

According to another embodiment of the invention, there is provided a method of chemical sensing comprising detecting changes of resistance to electric current in a 2DEG channel due to changes in stress in a III/N heterojunction caused by a change of the physical properties of a sensing layer, in a chemical sensor according to any of the embodiments herein described. The method of chemical sensing may advantageously comprise applying an electric current through the 2DEG channel such as to heat the surface of the flexible membrane to a predetermined temperature and thereby changing the sensing properties of the chemical sensor.

Monitoring for changes in resistivity may comprise generating a DC current within the two dimensional electron gas and monitoring at least one of the magnitude of the DC current and a DC voltage across the two dimensional electron gas. The III/N heterojunction structure may comprise a first layer of AlGaN and a second layer of GaN. The first layer of AlGaN may have a thickness in the range of 5-20 nm inclusive, or a thickness in the range of 6-10 nm inclusive.

In another aspect the invention relates to use of stress induced resistivity modulation of a two dimensional electron gas for chemical detection wherein the two dimensional electron gas is formed in a flexible membrane having a III/N heterojunction structure and the stress induced resistivity modulation is caused by a change in physical properties of a sensing material in the presence of one or more target chemicals.

The invention also relates to a method of manufacture of a chemical sensor such as described above. The method comprises: taking a multilayer structure comprising a III/V heterojunction formed on a substrate; thinning part of the structure so as to form a flexible membrane comprising the III/V heterojunction; and providing a sensing material on the flexible membrane, the sensing material being sensitive to one or more target chemicals so as to undergo a change in physical properties in the presence of said one or more target chemicals; wherein the sensing material is provided such that said change in physical properties of the sensing material imparts a change in stress within the heterojunction structure.

The step of thinning part of the structure to form a flexible membrane may comprise etching part of the substrate and/or the III/V heterojunction. Advantageously the method may comprise etching the substrate only. Conveniently the thinning step is performed such that the flexible membrane contacts the rest of the structure on all sides. In other words the method does not involve isolating any part of the membrane from the rest of the structure.

The step of providing the sensing material may comprise depositing a sensing material. The depositing step may be performed using printing techniques. Conveniently, the sensing material is deposited in a recess formed by the flexible membrane and the side walls of the rest of the structure.

BRIEF DESCRIPTION OF THE DRAWINGS

The invention will now be described by way of example only with respect to the following drawings, of which.

DETAILED DESCRIPTION

Figure 1:
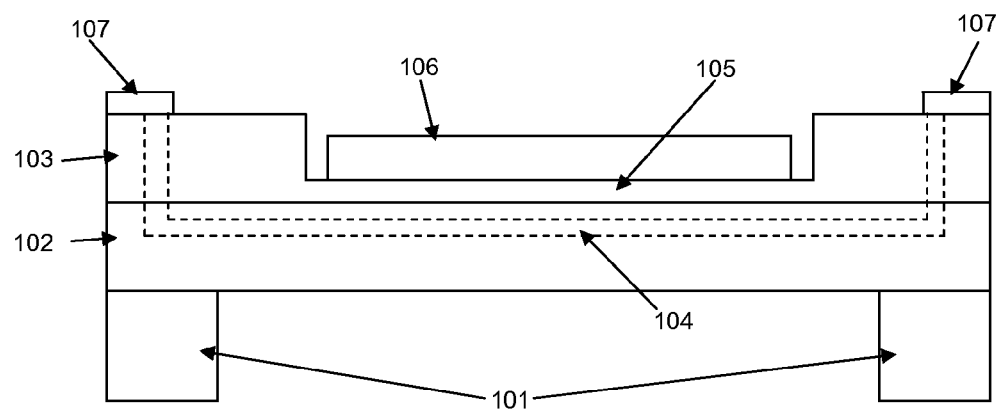
FIG. 1 shows a chemical sensor according to an embodiment of the invention.

FIG. 1 illustrates one embodiment of a chemical sensor according to an embodiment of the invention. The sensor is formed on a substrate 101 which may, for example, be a silicon wafer although any other suitable substrate could be used. The substrate may also comprise one or more layers such as buffer layers or etch stop layers on the silicon wafer. Supported on the substrate is a heterojunction of group III nitride materials. In this example the heterojunction comprises a layer of GaN 102 and a layer of AlGaN 103 arranged so as to form a two dimensional electron gas (2DEG) channel 104. A least part of the GaN layer 102 is freestanding with respect to the substrate, i.e. at least part of the GaN layer is not in direct contact with the substrate. As shown in FIG. 1 this may be achieved by a discontinuity in the substrate, i.e. the GaN layer is formed over a gap or cavity in the substrate. However other arrangements are possible, for example the GaN layer may be formed as a microbridge over the substrate.

The GaN layer 102 and AlGaN layer 103 form a flexible membrane in the region over the gap or cavity in the substrate, that is the GaN and AlGaN layers are able to bend/deform to a significant degree with respect to the supporting substrate 101. The thicknesses of the GaN layer 102 and AlGaN layer 103 may be chosen to provide sufficient flexibility of the membrane but also form a suitable 2DEG channel 104 within the flexible membrane. The GaN layer may, for example have a thickness in the range of 1-3 µm. The AlGaN layer 103 may be thinned in a certain the region of the membrane to provide a thin layer 105 within a thickness in the range of 6-10 nm.

In one embodiment, on top of the thin AlGaN layer 105 a layer of sensing material 106 may be deposited. The sensing material is chosen to be sensitive to one or more target chemicals, for instance a gas to be detected, and to undergo a change in properties in presence of the target chemical that leads to a lattice deformation in the underlying heterojunction. For example the sensing material may be a polymer material that absorbs the target chemical(s) leading to a volume expansion, i.e. swelling. Alternatively some sensing materials may exhibit a volume reduction in response to a target chemical or dissolve in the presence of the target chemical leading to a lattice deformation in the underlying heterojunction. Any material that exhibits a selective response to the target chemicals and can impart that response to the underlying heterojunction may be used. Examples of such materials are swellable polymers, for example poly(methyl methacrylate), acrylamide, acrylic acid, salts and esters of acrylic acid including sodium and sulfopropyl acrylates, 2-hydroxyethyl methacrylate; cellulose derivatives and hydrocolloids including alginate, chitosan, pectin, poly(ethylene oxide), carbopol, poly (vinyl alcohol); porous materials such as sodium carboxymethylcellulose, sodium starch glycolate, crosslinked poly (vinyl pyrrolidone); matrices of, for example, polymers containing micro or nanoparticles, colloids, crystals, for example zeolites, fibers, carbon nanotubes, metal particles; sol-gels, hydro-gels; any other porous and interconnected porous materials; polyelectrolytes; nanocomposites; ionic liquids; metals; metaloxides and combinations of these. In the example shown in FIG. 1 the sensing material 106 is deployed directly on the top of the thin AlGaN layer 105 but it will be appreciated that one or more other layers, such as adhesion promoters or protective layers may be used provided that the change in properties of the sensing material leads to a change in stress in the heterojunction.

Heterostructures formed in group III nitride materials exhibit spontaneous and piezoelectric polarization (which is much higher than the polarization in similar structures formed in group III/V materials). The ionic bonds of III-nitrides give rise to a macroscopic spontaneous polarization of the crystal lattice which changes abruptly at every interface. In addition, a superimposed piezoelectric polarization can appear due to mechanical distortion of the lattice, i.e. due to strain induced by the lattice misfit at the interface. The change in polarization P at the interface leads to a net bound polarization charge at the interface given by $\sigma = \nabla \cdot P$. If the polarization induced sheet charge density $\sigma$ is positive, free electrons provided by the background carrier concentration or by injection from metal contacts compensate for the polarization induced charge, giving rise to pronounced downward band bending and the formation of a 2DEG.

Deformation of the flexible membrane can therefore change the strain at the heterojunction interface and thus vary the piezoelectric polarization (e.g. due to pyro- and piezo-electric GaN/AlGaN properties, according to an embodiment). This change in polarization results in a change in the 2DEG density and hence the conductivity or resistivity of the 2DEG conductive channel. Thus the stress-induced piezo-resistive effect in the 2DEG channel 104 will reflect changes in the stress induced by the sensing material 106.

Figure 2:
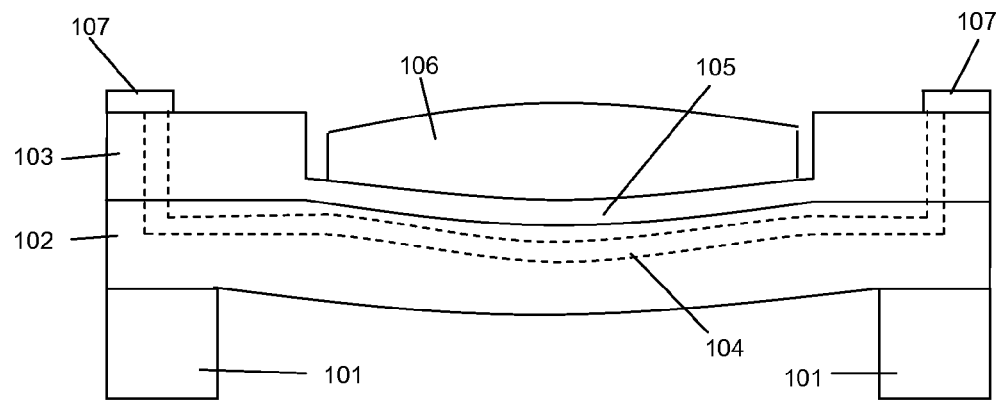
FIG. 2 illustrates how the sensor as shown in FIG. 1 reacts to a target chemical.

FIG. 2 illustrates how the sensor described above in relation to FIG. 1 may react in the presence of a target chemical. According to one embodiment, the target chemical may be absorbed by the sensing layer 106 which results in a volume change in the sensing layer, in this instance a swelling. The swelling of the sensing layer 106 creates a strain on the underlying flexible membrane. As the membrane is flexible and is freestanding with respect to the substrate, i.e. it is not constrained, the volume change of the sensing layer 106 will lead to deformation, i.e. bending, of the membrane. This deformation will result in a significant change in the piezo-electric polarization within the heterojunction and consequently result in a modulation of the resistivity of the 2DEG.

The 2DEG is connected to readout electrodes 107 as will be understood by one skilled in the art. The resistivity modulation of the 2DEG can be determined by any suitable method. For instance, a voltage could be applied across the readout electrodes 107 and the current measured. Alternatively, a known current may be driven through the 2DEG channel via the electrodes 107 and the resultant voltage measured. As the measurement is therefore direct electrical readout, and no electrical actuation is required, the sensor exhibits low power consumption, making it suitable for battery powered applications.

Typically the sensing material 106 will be deposited over the whole of the area of the flexible membrane so as to maximise the stress induced by the sensing material in the presence of the target chemical. However in some embodiments the sensing material may be deposited only in certain areas and arranged so as to impart the maximum change in stress.

As mentioned above the flexible membrane may be formed to be freestanding with respect to the substrate. For example the membrane could be formed as a beam or film which is supported at either side, i.e. a doubly clamped beam arrangement. In another embodiment however the flexible membrane does form a continuous structure with the substrate, i.e. the membrane is effectively supported at all sides as forms a flexible diaphragm type arrangement. In such an arrangement the membrane may have any shape, but a circular shape is advantageous in terms of ease of manufacture and allowing deformation to occur in all directions.

Figure 3:
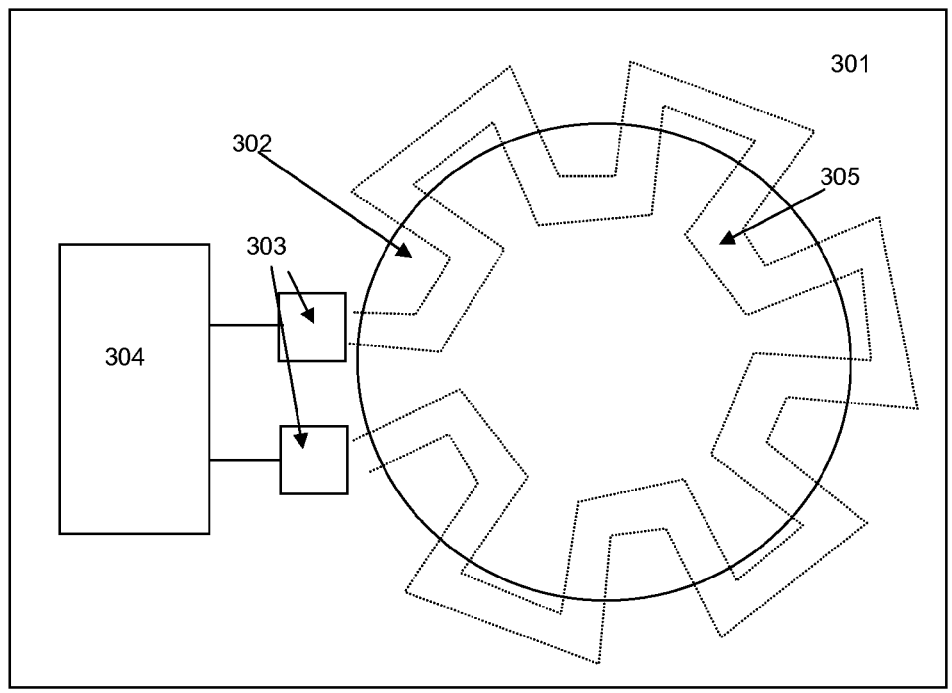
FIG. 3 illustrates a top view of a chemical sensor according to an embodiment of the invention.

In some embodiments the path of the 2DEG channel 104 may be deliberately arranged to run through the regions of the membrane that will experience the greatest stress due to the deformation caused by changes in the sensing layer. FIG. 3 shows a top view of a sensor according to an embodiment of the invention. FIG. 3 illustrates a substrate 301 with a flexible membrane 302 which is circular in shape and supported at all sides by the substrate. Such a structure could be formed by taking a complete substrate, depositing the III-nitride heterojunction and then back-etching part of the substrate to leave the membrane over a cavity.

FIG. 3 also shows readout electrodes 303, connected to readout circuitry 304. The readout circuitry 304 is illustrated as being on the same substrate 301 as the sensor but in some embodiments the readout circuitry may be provided on a separate substrate with a suitable electrical connection the electrodes 303. The electrodes 303 are coupled to the 2DEG 305. As shown, the path of the 2DEG is arranged to be serpentine and to stay mainly towards the edges of the membrane 302. As will be appreciated if the sensing material is disposed over the whole of the membrane 302 any volume changes will lead to a deformation which will concentrate the greatest strain towards the edges of the membrane. The meandering path of the 2DEG 305 thus ensures that any deformation of the membrane caused by the sensing material will result in significant resistivity modulation of the 2DEG.

The 2DEG-channels may be formed by a standard implantation process, using resist as a mask. By implantation the crystalline structure of the AlGaN/GaN interface at the depth of the 2DEG is disrupted by defects such that the formation of the 2DEG is inhibited.

The sensor may be initially fabricated in a mechanically unstressed state as in an embodiment shown in FIG. 1. In another embodiment however the sensor may be fabricated with the membrane in a pre-stressed state, which may be, for example, tensile and/or compressive stress.

Figure 4:
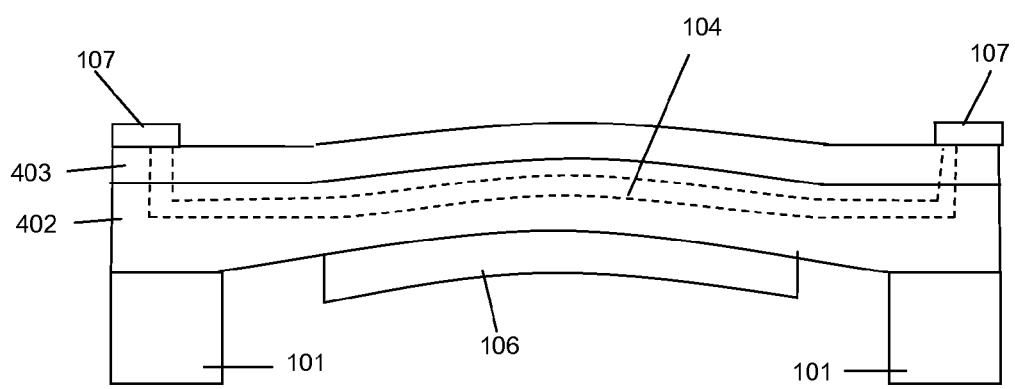
FIG. 4 illustrates a chemical sensor with a pre-stressed membrane.

FIG. 4 shows a sensor according to another embodiment of the invention. FIG. 4 shows the sensor as fabricated where similar components are given the same reference numerals as in FIG. 1. In the sensor shown in FIG. 4 a GaN layer 402 and AlGaN layer 403 are supported by the substrate 101 in a pre-stressed manner such that the membrane has an inherent deformation. This has the advantage that in case of a contraction of the sensing layer, the membrane is returned to a undeformed state.

As shown in FIG. 4 the layer of sensing material 106 may also be located on the underside of the flexible membrane, i.e. the same side as the substrate. Such an arrangement can aid in manufacture when the membrane is a continuous structure with the substrate as effectively the substrate and membrane form a well. Thus the sensing material can be deposited more easily using printing techniques and/or without loss of material due to layout dependent run off.

A sensing layer on the underside of the flexible membrane also means that the sensing layer is on the opposite side of the device to the readout electrodes. Thus the readout electrodes and any connected readout circuitry may be suitably protected from the sensing environment. This may be of particular importance if the sensor is to be used in liquid environments for example.

In the embodiment of FIG. 4 the AlGaN layer has not been etched to form an ultrathin layer and thus the device shown in FIG. 4 may be fabricated with a single etching step. Of course the AlGaN layer 403 may be etched if required to tune the resistivity of the 2DEG channel and provide enhanced sensitivity to proximal charges or surface dipoles. The combination of back-etched and non-back etched structures may provide additional information over the type of gas/vapour that is detected.

Figure 5A:
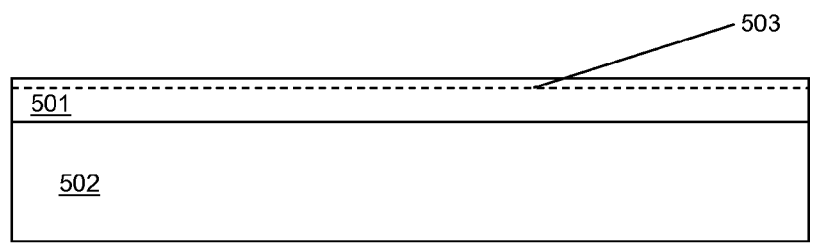
FIGS. 5a-e illustrate the steps of manufacturing a sensor according to an embodiment of the invention.

FIGS. 5a-5e show one example of a suitable manufacturing process for manufacturing a sensor such as the one shown in FIG. 4. Referring to FIG. 5a the AlGaN/GaN layer stack 501 was grown by metal-organic-chemical-vapour-deposition epitaxial on highly resistive Si (111) substrates 502. The layer stack typically comprises an AlN nucleation layer, an AlGaN intermediate layers, a GaN buffer layer and an $Al_xGa_yN$ barrier layer which is preferably capped after growth with an in-situ deposited $Si_3N_4$ or GaN layer (individual layers not shown). The 2DEG channel 503 is formed on the GaN/AlGaN interface. The stack allows the spontaneous formation of a 2DEG (unnumbered) close to the Al0.3GA0.7N/GaN interface.

Figure 5B:
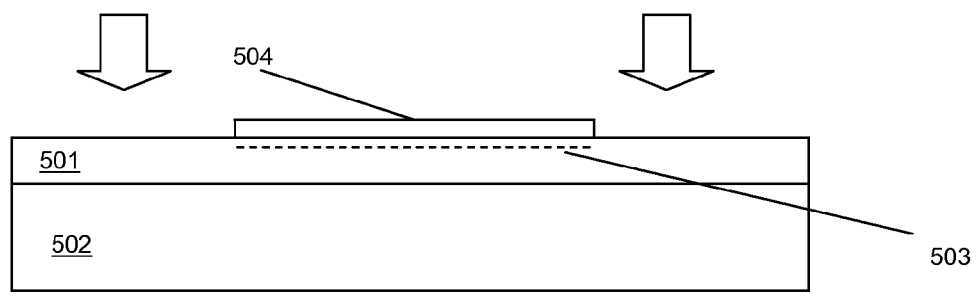

As shown in FIG. 5b a 2DEG channel or channels 503 can be patterned by a standard implantation process, using a lithographical resist mask 504. The 2DEG is removed by the implantation process in the outside of the channel. After implantation, the resist mask 504 is removed.

Figure 5C:
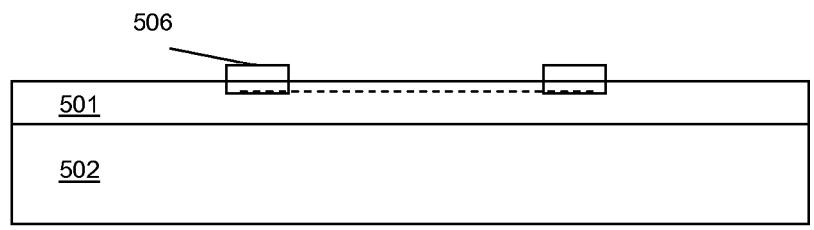
Figure 5D:
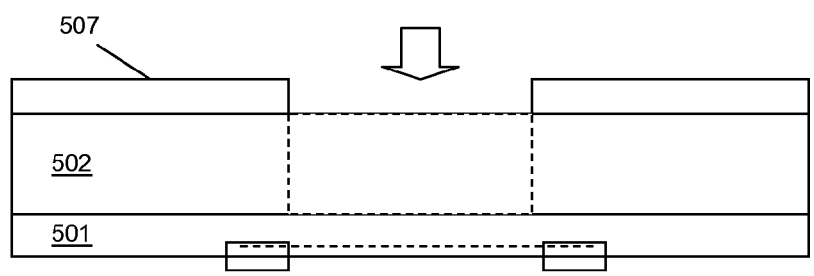
Figure 5E:
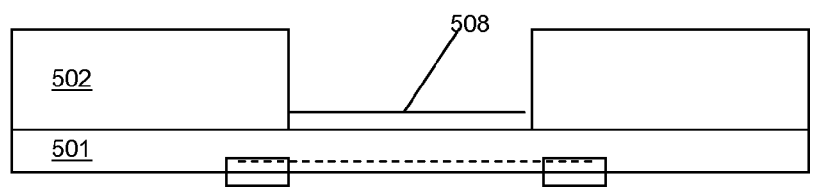

The ohmic contacts 506, in FIG. 5c, can be fabricated by a standard lift-off process, including deposition of 20 nm Ti/40 nm Al/25 nm Mo/50 nm Au, followed by annealing at 800° C. in a nitrogen atmosphere. Other metal stack can be used. Metal can be patterned also by other process than lift-off.

Although not shown in FIG. 5, if required the AlGaN-layer (including the top cap layer) can be etched back (ultrathinned) using inductively coupled plasma based reactive ion etching (ICP-RIE) or ion milling using a resist as a mask, or by controlled oxidation/etching process.

The suspended membrane can be formed by removing the Si substrate 502 in the membrane area, for example using the Bosch process. A silicon nitride, silicon oxide or a resist can be used as a mask 507.

Finally the resist 507 can be removed and sensing material 508 deposited in the recess formed in the substrate 502. As the membrane area is continuously connected to the substrate side walls the sensing material 508 is held in place during deposition.

It will be appreciated that at least some of the steps described above in relation to FIGS. 5a-e may be performed in a different order depending on the manufacturing processes used.

According to further embodiments, heating of the chemical sensor to a certain temperature may be performed by applying a certain voltage to the ohmic contacts 506 or readout electrodes 107, 303. Alternatively, a certain current may be driven through the 2DEG channel via those ohmic contacts 506 or readout electrodes 107, 303. The 2DEG channel, in such embodiments, may be designed such as to allow reaching such temperature of the sensor when a certain current or voltage is applied.

The invention claimed is:

1. A chemical sensor comprising:
a flexible membrane comprising a III/N heterojunction structure configured so as to form a two dimensional electron gas channel within said structure; and
a sensing material disposed on at least part of said flexible membrane, the sensing material being sensitive to one or more target chemicals such that it would undergo a change in physical properties in the presence of said one or more target chemicals;
wherein the sensing material is coupled to said heterojunction structure such that said change in physical properties of the sensing material would impart a change in stress within the heterojunction structure which would modulate the resistivity of the two dimensional electron gas channel,
wherein the change in physical properties of the sensing material is a volume change due to absorption of the one or more target chemicals or a change in structure or amount of the sensing material due to absorption, dissolution, or both absorption and dissolution of the sensing material in the presence of the one or more target chemicals.

2. The chemical sensor as claimed in claim 1 wherein said flexible membrane is partially suspended relative to a substrate such that it can freely bend.

3. The chemical sensor as claimed in claim 2 comprising side walls which extend from said substrate and connect to said flexible membrane at its edges such that the flexible membrane is suspended relative to the substrate.

4. The chemical sensor as claimed in claim 1 further comprising readout electrodes and circuitry configured for determining the resistance, the conductivity, or both the resistance and conductivity of the two dimensional electron gas channel.

5. The chemical sensor as claimed in claim 4 configured for detecting the presence of one or more target chemicals by detecting changes in electrical resistance, conductivity, or both resistance and conductivity of the two dimensional electron gas channel.

6. The chemical sensor as claimed in claim 4, wherein said two dimensional electron gas channel is designed with predetermined dimensions such as to ensure a certain heating temperature of the flexible membrane when a certain current is applied across said channel.

7. The chemical sensor as claimed in claim 4 wherein the readout electrodes are disposed such that the two dimensional electron gas channel provides a conductive path between said readout electrodes, and wherein the circuitry comprises circuitry configured to generate a DC current between said readout electrodes and monitor at least one of the magnitude of said DC current and a DC voltage between the readout electrodes.

8. The chemical sensor as claimed in claim 1, wherein said the two dimensional electron gas channel is formed along a path within the flexible membrane which runs through a region of the membrane that would experience mechanical stress in response to the change in physical properties of the sensing material.

9. The chemical sensor as claimed in claim 1, wherein said sensing material is at least one layer of sensing material located on a top or a bottom side of the flexible membrane.

10. The chemical sensor as claimed in claim 1 wherein said III/N heterojunction structure comprises a first layer of AlGaN and a second layer of GaN.

11. The chemical sensor as claimed in claim 10 wherein said first AlGaN layer has a thickness in the range of 6 to 10 nm inclusive.

12. The chemical sensor as claimed in claim 10 wherein said second GaN layer has a thickness in the range of 500 nm to 3 μm inclusive.

13. The chemical sensor as claimed in claim 1 wherein said flexible membrane is circular in shape.

14. The chemical sensor as claimed in claim 1 wherein in the absence of any of said one or more target chemicals, said sensing material would cause the flexible membrane to be in a mechanically-induced stressed state.

15. A method of chemical sensing comprising detecting changes of electrical resistance, conductivity, or both resistance and conductivity of a two dimensional electron gas channel in a chemical sensor according to claim 1.

16. The method of chemical sensing of claim 15 further comprising applying an electric current through the two dimensional electron gas channel such as to heat the surface of the flexible membrane to a predetermined temperature and thereby changing the sensing properties of the chemical sensor.

17. A method of sensing a target chemical, the method comprising
proving a chemical sensor according to claim 1;
exposing the chemical sensor to the target chemical; and
detecting a change in electrical resistance, electrical conductivity, or both electrical resistance and conductivity of the two dimensional electron gas channel.

18. The method of claim 17, further comprising applying an electric current through the two dimensional electron gas so as to heat the surface of the flexible membrane.

19. A chemical sensor comprising:
a flexible membrane comprising a III/N heterojunction structure configured so as to form a two dimensional electron gas within said structure, the flexible membrane being free-standing over a supporting substrate; and a sensing material sensitive to one or more target chemicals;

configured such that a change in stress within the heterojunction structure would modulate the resistivity of the two dimensional electron gas;

wherein the sensing material is a layer of material different from the substrate which is disposed on at least part of said flexible membrane; and the sensing material would undergo a change in physical properties in the presence of said one or more target chemicals and would impart a change in stress within the heterojunction structure, wherein the change in physical properties of the sensing material is a volume change due to absorption of the one or more target chemicals or a change in structure or amount of the sensing material due to dissolution, absorption, or both absorption and dissolution of the sensing material in the presence of the one or more target chemicals.

* * * * *